(12) United States Patent
Salkola et al.

(10) Patent No.: US 11,980,422 B2
(45) Date of Patent: May 14, 2024

(54) ALIGNMENT MEANS OF MEASUREMENT INSTRUMENT

(71) Applicant: ICARE FINLAND OY, Vantaa (FI)

(72) Inventors: Mika Salkola, Espoo (FI); Antti Jaatinen, Leppävirta (FI); Kati Stranius, Kuopio (FI); Mertsi Haapalainen, Kuopio (FI)

(73) Assignee: ICARE FINLAND OY, Vantaa (FI)

( * ) Notice: Subject to any disclaimer, the term of this patent is extended or adjusted under 35 U.S.C. 154(b) by 605 days.

(21) Appl. No.: 17/166,396

(22) PCT Filed: Sep. 4, 2019

(86) PCT No.: PCT/FI2019/050627
§ 371 (c)(1),
(2) Date: Feb. 3, 2021

(87) PCT Pub. No.: WO2020/053476
PCT Pub. Date: Mar. 19, 2020

(65) Prior Publication Data
US 2021/0298598 A1    Sep. 30, 2021

(30) Foreign Application Priority Data

Sep. 11, 2018 (FI) .................................. 20185754

(51) Int. Cl.
*A61B 3/16* (2006.01)
*A61B 3/00* (2006.01)
(Continued)

(52) U.S. Cl.
CPC ............ *A61B 3/165* (2013.01); *A61B 3/0008* (2013.01); *A61B 3/152* (2013.01); *G02B 6/4226* (2013.01)

(58) Field of Classification Search
CPC ........ A61B 3/165; A61B 3/0008; A61B 3/152; A61B 3/16; G02B 6/4226
(Continued)

(56) References Cited

U.S. PATENT DOCUMENTS 10,058,245 B2    8/2018  Herranen et al.
2005/0046794 A1  3/2005  Silvestrini et al.
(Continued)

FOREIGN PATENT DOCUMENTS

EP    2090221 A1    8/2009
EP    2997881 A1    3/2016
(Continued)

OTHER PUBLICATIONS

Finnish Registration and Registration Office, Search Report, U.S. Appl. No. 20/185,754, dated Apr. 9, 2019, 2 pages.
(Continued)

*Primary Examiner* — Mohammed A Hasan
(74) *Attorney, Agent, or Firm* — Ziegler IP Law Group

(57) ABSTRACT

An alignment means of a measurement instrument includes a housing an optical component having a principal axis in a direction parallel to a desired alignment; a first light source positioned at a first distance S1 from the optical component and at a first height h1 from the principle axis; a second light source positioned at a second distance S2 from the optical component and at a second height h2 from the principle axis; and an angle barrier means arranged between the optical component, and the first and second light sources. The housing, the optical component, and the angle barrier means are arranged to block visibility of the first light source along the principal axis at a distance superior to d1'; and block visibility of the second light source along the principal axis at a distance smaller than d2, wherein d2 is smaller than d1'.

14 Claims, 5 Drawing Sheets

(51) Int. Cl.
*A61B 3/15* (2006.01)
*G02B 6/42* (2006.01)

(58) Field of Classification Search
USPC .......................................................... 351/205
See application file for complete search history.

(56) References Cited

U.S. PATENT DOCUMENTS

| | | |
|---|---|---|
| 2005/0117782 A1 | 6/2005 | Imaoka et al. |
| 2010/0069373 A1* | 3/2010 | Han ................... C07D 243/24 540/509 |
| 2010/0069737 A1 | 3/2010 | Jinde et al. |
| 2010/0152847 A1* | 6/2010 | Padrick .................. A61B 3/13 623/6.11 |
| 2011/0032481 A1 | 2/2011 | Uchida et al. |
| 2014/0275935 A1* | 9/2014 | Walsh .................. A61B 3/0083 600/398 |
| 2016/0174838 A1 | 6/2016 | Herranen et al. |
| 2016/0299058 A1* | 10/2016 | Li ............................ A61B 3/10 |
| 2017/0311796 A1* | 11/2017 | Walsh .................. A61B 3/0058 |
| 2018/0064337 A1* | 3/2018 | Abramoff ................ A61B 3/12 |
| 2018/0220888 A1 | 8/2018 | Tumlinson et al. |

FOREIGN PATENT DOCUMENTS

| | | |
|---|---|---|
| JP | H03176023 A | 7/1991 |
| JP | 2000014643 A | 1/2000 |
| JP | 2001017394 A | 1/2001 |
| JP | 2002119483 A | 4/2002 |
| JP | 2007513703 A | 5/2007 |
| JP | 2011036273 A | 2/2011 |
| JP | 2016524935 A | 8/2016 |
| WO | 2005058130 A2 | 6/2005 |

OTHER PUBLICATIONS

PCT, Notification of Transmittal of The International Search Report and The Written Opinion of The International Searching Authority, or The Declaration, Application No. PCT/FI2019/050627, dated Nov. 21, 2019, 14 pages.
Japan Patent Office, Notice of Allowance, Application No. 2021510718, dated Nov. 5, 2016, 3 pages.
Japan Patent Office, Notification of Ground of Rejection, Application No. 2021-510718, dated Jul. 6, 2023, 4 pages.

* cited by examiner

ALIGNMENT MEANS OF MEASUREMENT INSTRUMENT

TECHNICAL FIELD

The present disclosure relates generally to optics; and more specifically, to alignment means of measurement instruments.

BACKGROUND

Eyes are one of the most sensitive parts of human body and require extreme care and precautions. However, even with such extreme care and precautions, eyes tend to suffer a variety of ailments due to various factors like ageing, pollution, accidental damage and so forth. In such instances, eyes go through optometric and/or ophthalmic procedures such as retinal examinations, tonometry, eye surgery and so forth for an examination and proper treatment thereof. Such optometric and ophthalmic procedures are performed using measurement instruments. Furthermore, the measurement instruments used in the optometric and ophthalmic procedures require a desired alignment with respect to the eyes to achieve accurate results.

Presently, the desired alignment of the eyes with the measurement instruments is achieved by manually moving the instrument and/or by changing a position of the eyes. The instrument and/or the eyes are moved in a direction closer or away from each other in order to achieve the desired alignment. Many of the measurement instruments are hand-held and require an individual to achieve the desired alignment by himself. Alternatively, the measurement instruments are associated with a support and are moved to achieve the desired alignment based on a feedback from the individual.

However, presently used alignment means (namely, procedure) for the measurement instruments face several challenges. Such means are not user friendly as they require multiple feedbacks (namely, inputs) and manual effort from the individual. Additionally, the feedbacks are prone to error and can lead to a misalignment of the instrument. Furthermore, such alignment means are time consuming and inefficient and lead to delayed and substantially inaccurate results. Furthermore, such alignment means are unable to satisfactorily ensure the desired alignment. In other words self-alignment of a measurement instrument is difficult.

Therefore, in light of the foregoing discussion, there exists a need to overcome the aforementioned drawbacks associated with conventional alignment means for measurement instruments.

SUMMARY

The present disclosure seeks to provide an alignment means of a measurement instrument. The present disclosure also seeks to provide a measurement instrument comprising an alignment means. The present disclosure seeks to provide a solution to the existing problem of manual, time consuming process of alignment of a user's eye with the measurement instrument. An aim of the present disclosure is to provide a solution that overcomes at least partially the problems encountered in the prior art, and provides an easy to implement, efficient, robust, faster alignment means for achieving a desired alignment with the measurement instrument.

In one aspect, an embodiment of the present disclosure provides an alignment means of a measurement instrument, the alignment means comprising:
a housing;
an optical component having a principal axis in a direction parallel to a desired alignment, the optical component being configured such that an eye of the user is to be aligned with the principal axis of the optical component;
a first light source positioned at a first distance S1 from the optical component and at a first height h1 from the principle axis;
a second light source positioned at a second distance S2 from the optical component and at a second height h2 from the principle axis; and
an angle barrier means,
wherein the optical component comprises a focal point, wherein the first and second light sources are positioned between the optical component and the focal point; and
wherein the housing, the optical component, and the angle barrier means are arranged to:
block visibility of the first light source along the principal axis at a distance superior to d1'; and
block visibility of the second light source along the principal axis at a distance smaller than d2, wherein d2 is smaller than d1';
wherein d1' and d2 are distances from the optical component.

In another aspect, an embodiment of the present disclosure provides a measurement instrument comprising an alignment means.

Embodiments of the present disclosure substantially eliminate or at least partially address the aforementioned problems in the prior art, and enables an effortless, substantially accurate, robust and efficient alignment means of achieving a desired alignment of a user with a measurement instrument.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1:
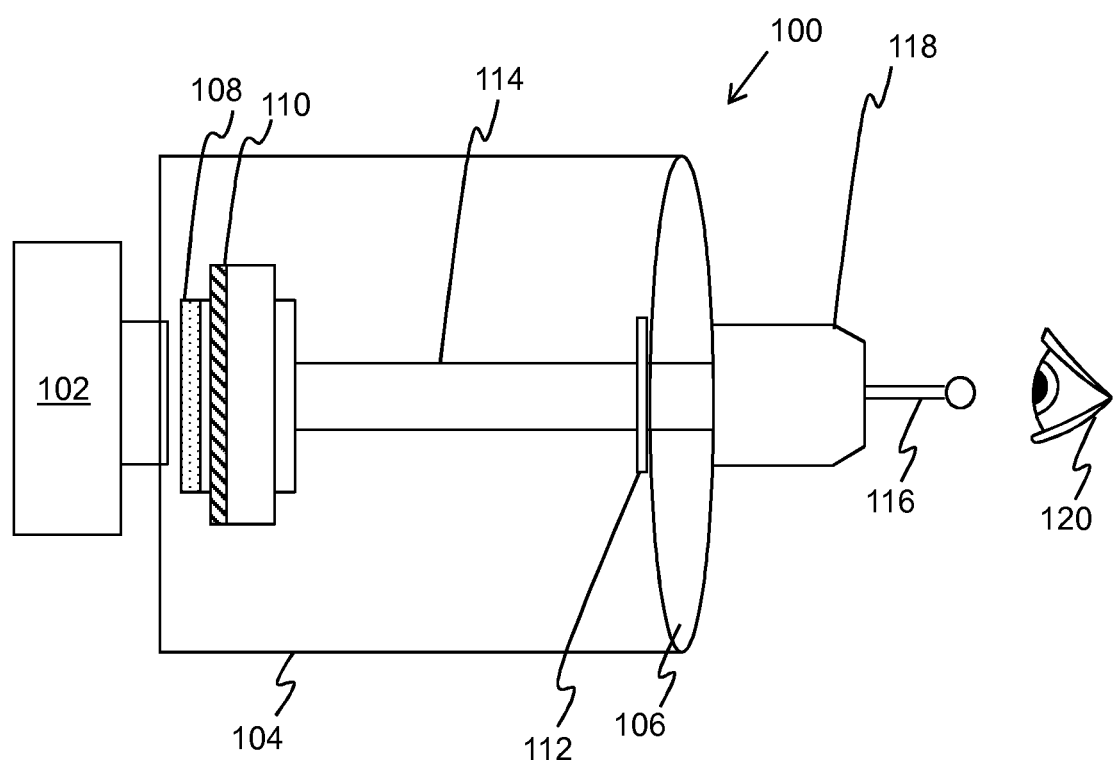
FIG. 1 is a schematic illustration of an alignment means of a measurement instrument, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an alignment means of a measurement instrument, the alignment means comprising:
 a housing;
 an optical component having a principal axis in a direction parallel to a desired alignment, the optical component being configured such that an eye of the user is to be aligned with the principal axis of the optical component;
 a first light source positioned at a first distance S1 from the optical component and at a first height h1 from the principle axis;
 a second light source positioned at a second distance S2 from the optical component and at a second height h2 from the principle axis; and
 an angle barrier means,
  wherein the optical component comprises a focal point, wherein the first and second light sources are positioned between the optical component and the focal point; and
  wherein the housing, the optical component, and the angle barrier means are arranged to:
   block visibility of the first light source along the principal axis at a distance superior to d1'; and
   block visibility of the second light source along the principal axis at a distance smaller than d2, wherein d2 is smaller than d1';
  wherein d1' and d2 are distances from the optical component.

The present disclosure provides an alignment means for achieving a desired alignment between the measurement instrument and a user thereof. The alignment means disclosed herein provides an efficient, seamless, robust, faster and optimised means for achieving the desired alignment. Moreover, an alignment means disclosed herein is easy to implement. In addition, the present disclosure can be implemented with existing optical and non-optical components. Furthermore, the alignment means substantially reduces dependency on user's feedback for achieving the desired alignment between the measurement instrument and the user thereof. Notably, the alignment means disclosed herein reduces manual effort required by the user to achieve the desired alignment. Therefore, a reduced requirement of feedback and manual effort by the user substantially reduces a probability of error in achieving the desired alignment. Furthermore, the measurement instrument comprising the alignment means as disclosed in the present disclosure provides an approach for achieving the desired alignment that is easy to understand and implement by the user.

Pursuant to embodiments of the present disclosure, the alignment means is configured to facilitate in achieving a desired alignment of the measurement instrument with respect to a user. Specifically, the desired alignment refers to a substantially accurate positioning of user's eye with respect to the measurement instrument for proper functioning of the measurement instrument. Notably, the alignment means facilitates in achieving the substantially accurate positioning of user's eye with respect to the measurement instrument by adjusting at least one of: a direction of viewing of the user, distance of the user (specifically, the user's eye) from the measurement instrument, a tilting angle of the user and a vertical and horizontal alignment of the user's eye.

Furthermore, the measurement instrument refers to a device operable to measure parameters of an eye, view an image and/or object, analyze light waves and so forth. In an example, the measurement instrument is operable to measure eye pressure i.e. the measurement instrument is an instrument for measuring a pressure of an eye. Moreover, the user may be an entity (for example, an individual, an instrument, a processing device and so forth) that needs an output from the measurement instrument for tasks like eye surgery, pressure measurement and so forth. The user requires the desired alignment with the measurement instrument for a correct functioning thereof. Specifically, the correct functioning of the measurement instrument relates to ability of the measurement instrument to perform specific tasks such as measure parameters of an eye, view an image, analyzing light waves and the like and provide an accurate output to the user. The user requires an accurate positioning with respect to the measurement instrument for obtaining a correct output of the tasks performed by the measurement instrument. Moreover, the user uses the alignment means to achieve the desired alignment with the measurement instrument.

The optical component has a principal axis in a direction parallel to a desired alignment, i.e. the principal axis of the optical component is parallel with the optical axis of the eye of the user. Thus, the optical component is configured such that an eye of the user is to be aligned with the principal axis of the optical component, when the measurement instrument is being used.

The present alignment means is connectable to a measurement instrument in such a way that the principal axis of the optical element coincides with a relevant axis of the measurement instrument. For example, in case the measurement instrument is a tonometer, the principal axis of the optical element coincides with the ejection direction (axis) of the tonometer probe. The alignment means can be a detachable or an integral part of the measurement instrument.

Optionally, the alignment means is operatively coupled with the measurement instrument by way of a supporting means. The supporting means is a cylindrical or cuboidal structure that provides support to the alignment means.

Optionally, the alignment means is permanently attached with the measurement instrument and cannot be detached from the measurement instrument. In another instance, the alignment means can be detachably coupled to the measurement instrument thus the alignment means is removable. In such an instance the detachable coupling of the alignment means with the measurement instrument allows the alignment means to be attached and used with another measurement instrument.

Throughout the present disclosure, the term "alignment means" relates to an arrangement associated with the measurement instrument. The alignment means comprises a plurality of optical and non-optical components for achieving the desired alignment. The accurate positioning of the measurement instrument and the user's eye with respect to each other provides the desired alignment therebetween.

As mentioned previously, the alignment means of the measurement instrument comprises the housing. In addition, the housing is configured to accommodate optical and non-optical components of the alignment means. The housing is further configured to keep the components of the alignment means at a respective position thereof within the alignment means. Additionally, the housing provides a protection to the alignment means from an external interference. Furthermore, the housing is also configured to protect the components of the alignment means from damages caused by an external cause such as an accidental damage. The housing has a first end and a second end, wherein the first end faces the user's eye and the second end is towards the measurement instrument.

Optionally, a body of the housing is opaque or non-transparent in nature. The body of the housing can be manufactured from a metallic or non-metallic material. Additionally, the housing has hollow and regular geometric shape such as cubical, cuboidal, spherical, and so forth. Alternatively, the housing has an irregular geometric shape.

The alignment means comprises the optical component. The optical component is a refractive medium that allows light to pass therethrough. The optical component being a refractive medium changes path of the light passing therethrough. Moreover, the optical lens is positioned at a first end of the housing. Additionally, the optical lens has a principal axis (namely, an optical axis) in a direction parallel to the desired alignment. The principal axis refers to an axis passing through an optical center (namely, a geometrical center) of the optical component and joining the two centers of curvatures of the optical component.

Furthermore, the alignment means comprises the first light source and the second light source. The first and second light sources is configured to emit light towards the optical component. The first light source is positioned at the first distance S1 from the optical component and at the first height h1 from the principle axis. The housing encompasses the first light source within the hollow structure thereof. Additionally, the first light source is positioned towards the second end of the housing. Such positioning of the first light source and the optical component allows light rays from the first light source to be projected on the optical component and pass therethrough.

Moreover, the alignment means comprises the second light source, wherein the second light source is positioned at the second distance S2 from the optical component and at the second height h2 from the principle axis. Additionally, the second light source is positioned towards the second end of the housing. Such positioning of the second light source and the optical component allows light rays from the second light source to be projected on the optical component and pass through it.

Optionally, the first and second light sources are positioned above the principal axis at heights h1 and h2 respectively. Alternatively, optionally, the first and second light sources are positioned below the principal axis.

Optionally, the first distance S1 and the second distance S2 are equal. Therefore, the first light source and the second light source are positioned at an equal distance from the optical component.

It will be appreciated that the first height h1 and the second height h2 are unequal. In other words, the first light source and the second light source are positioned at different heights with respect to each other. Notably, since the first height h1 and the second height h2 are unequal therefore any one of the first light source and the second light source do not block other's visibility. Therefore, visibility of both the first light source and the second light source allows for a correct functioning of the alignment means. Specifically, the first height h1 is lesser or greater than the second height h2. However, throughout the present disclosure, for sake of simplicity and clarity the first height h1 is considered to be greater than the second height h2.

Optionally, the alignment means further comprises a third light source arranged at a distance S3 from the optical component and at a third height h3 from the principal axis. The housing further encompasses the third light source. Additionally, the third light source is positioned towards the second end of the housing. Such positioning of the third light source and the optical component allows light rays from the third light source to be projected on the optical component and pass through it.

Optionally, the third light source is positioned at any one of the positions: above the first and second light sources, below the first and the second light sources or between the first and the second light sources.

Optionally, at least one of the first, second and optional third light sources is a circular light source. The first, second and optional third light sources are in form of rings, circular disks. Additionally, the first, second and optional third light sources are positioned in a consecutive order. In this optional an embodiment the heights (h1, h2, h3) corresponds to radius of the circular light source in respect to the principal axis. i.e. the first circular light source has radius of h1, the second circular light source has radius of h2 and the third circular light source has radius of h3.

Furthermore, optionally, each of the first, second and optional third light sources are arranged to provide a differently colored light. The different color of each of the first, second and optional third light sources provide a unique identification thereto. Moreover, the different color of first, second and optional third light sources allow the user for an easier identification of a source of light coming from any one of the first, second and optional third light sources. In an example, the first light source may emit a blue light, the second light source may emit a green light and the third light source may emit a yellow light.

Optionally, at least one of the first, second and optional third light sources is a blinking light source. In addition, blinking of any one of the first, second and optionally third light source allows the user to identify a correct source of the light. Beneficially, such blinking of the first, second and optional third light sources allows for an easier and faster achievement of the desired alignment.

More optionally, the first, second and optional third light sources are implemented by way of a light emitter and a light guide. The light emitter is a source of light that is configured to emit at least one ray of light towards the optical component. Additionally, the light emitter is associated with a switch configured to change a state (ON/OFF) thereof. Furthermore, the light emitter is attached with a power source configured to provide power to the light emitter for functioning thereof. In an example, the light emitter is a light emitting diode. The light emitting diode (LED) is a two lead semi-conductor light source. Beneficially, such high brightness of the first, second and optional third light sources allows a visibly challenged user to identify the first, second and optional third light sources.

Furthermore optionally, the light emitter is associated with the light guide, that allows for achieving a proper functioning of the first, second and optional third light sources. Additionally, the light guide is configured to direct light from the light emitter towards the optical component. The light guide prevents an early scattering of the light from the light emitter. In an example, the light guide is one of a circular light guide, a triangular light guide, an oval light guide, a square light guide, a line light guide. The shape of the light guide associated with the light emitter can be chosen based on a requirement by the user of the aforementioned measurement instrument. In addition, the light guide is operable to control a travelling path of the light emitted from the light emitter towards the optical component.

Optionally, the optical component is a lens for example, a converging lens, a diverging lens, combinational lens, a Fresnel lens, and the like. The optical component has an optical center at a geometrical center thereof. In addition, the optical component has a principal axis running through the optical center thereof. Furthermore, the principal axis of the optical component includes at least one focal point thereon. Moreover, the optical component forms virtual image of the first, second and optional third light source based on a position thereof with respect to the at least on focal point. Notably, a virtual image formed by a lens relates to an image formed when light rays coming from the first and second light source do not intersect but appear to intersect when extended backwards. These images formed are apparent in nature.

It will be appreciated that the optical component is any lens that is operable to create a virtual image of the first and second light sources. However, throughout the disclosure the optical component has been assumed to be a converging lens for sake of simplicity and understanding.

It will be appreciated that throughout the present disclosure "viewing the first light source" relates to viewing of virtual image of the first light source through the optical component and "viewing the second light source" relates to viewing of virtual image of the second light source through the optical component.

Optionally, the first distance S1 of the first light source and the second distance S2 of the second light source is less than a distance between the optical center and focal point of the optical component. Furthermore, the first distance S1 and the second distance S2 may vary depending upon a type of the optical component. Specifically, the position of the first and second light sources are varied based on a property of the optical component for creating virtual images.

Optionally, in an implementation of the present disclosure, the optical component is a converging lens. The converging lens is operable to create a virtual image when the object is placed between focal point and the optical center. The converging lens is configured by applying thin lens formula (namely, lens equation). Specifically, the thin lens formula states that a sum of reciprocal of object distance and reciprocal of image distance is equal to reciprocal of focal length, wherein the focal length refers to a distance between optical center of the optical component and the focal point thereof. As mentioned previously, the first and the second light source is positioned between the optical center and the focal point of the optical component. Therefore, the optical component creates a virtual image of the first and second light source behind the focal point. The virtual image of the first light source can be seen by the user through the optical component. The virtual image of the first light source is visible until a distance d1' from the optical center along the principal axis, the distance d1' being a distance from the optical component. Similarly, the virtual image of the second light source can be seen by the user through the optical component. The virtual image of the second light source is visible after a distance d2 along the principal axis through the optical component until a distance d2', wherein distance d2 is a distance from the optical component. Notably, the virtual images of the first and second light sources are viewed by the user from a first end of the housing when viewed through the optical component.

The optical component comprises a focal point, wherein the first, second and optional third light sources are positioned between the optical component and the focal point. The focal point (namely, focus) of the optical component lies on the principal axis. It is to be understood that the first distance S1, the second distance S2 and the third distance S3 is less than a distance between the optical center of the optical component and the focal point. Specifically, the distance between the optical center of the optical component and the focal point forms the focal length of the optical component. Notably, the virtual image of the first, second and optional third light sources is formed towards a second end of the housing. Consequently, the virtual images of the first, second and optional third light sources are visible to the user through the optical component. The technical effect of this is that such a positioning of the first and the second light sources between the optical component and the focal point facilitates clear visibility of the light sources to the user even when the user's eye is in close proximity of the apparatus. Moreover, there is no blurring effect that is produced. The blurring effect leads to inaccurate positioning of the measurement instrument with respect to the user's eye. If the measurement instrument is positioned inaccurately, the measurement device will produce wrong results and might be harmful for the user. Indeed, positioning of the light sources between the optical component and the focal point enables an accurate positioning of the measurement instrument with respect to the user's eye.

As mentioned previously, the alignment means further comprises the angle barrier means. The angle barrier means is a non-transparent piece of a metallic or non-metallic medium. Furthermore, the angle barrier means is configured to block, allow, and/or change a path of the light coming from the first, second and optional third light source.

Optionally the angle barrier means are arranged between the optical component, and the first and second light sources. Alternatively the optical component is arranged between the angle barrier means and the first and the second light sources. Overall the angle barrier means are arranged in a way that it can block optical path from the light source to an eye of user of the measurement instrument. In essence the angle barrier can be in either side of the optical component. In addition, if the optical component comprises two or more lenses the angle barrier can be arranged between two lenses.

Optionally, the angle barrier means has a height smaller than the optical component that allows for visibility of the virtual images of the first, second and optional third light sources. The angle barrier means comprises at least one of a: circular shape, rectangular shape, a polygonal shape. The angle barrier means can be an angle barrier disk. The angle barrier means can be also others structural component arranged in the optical path between the light source(s) and eye of the user. As on example a part of the housing can function as the angle barrier means. Optionally/additionally a supporting structure can function as the angle barrier means.

Alternatively, optionally, the angle barrier means has a height equal or greater to the optical component. In such an instance, the angle barrier means has cut-outs therein that allows lights emanating from the first, second and optional third light source to pass therethrough. In addition, such cut-outs on the angle barrier means create patterns of lights that is viewed by the user through the optical component. In an example, the user may view a virtual image of a specific pattern of light for achieving the desired alignment by way of the alignment means.

Optionally, the alignment means comprises a probe attached to a supporting structure. The supporting structure is operably attached with the housing and provides a supporting structure for the alignment means. In addition, the probe attached to the supporting structure is positioned outside the housing. Additionally, the probe is positioned after the optical component towards the first end of the housing. The probe is arranged to move in a forward and backward direction inside the supporting structure for measuring properties of the user's eye. In an example implementation the probe is arranged to hit (impact) users eye and movement of the probe before, during and/or after the impact is measured. The measurement results are analyzed to derive pressure of the eye. In said measurement example proper alignment and proper distance from the users eye is needed in respect to the measurement instrument (and thus to the probe). In additional embodiment supporting structure (or part of the supporting structure) for attaching the probe can function as the angle barrier means. In another example implementation there can be for example water pulse provided towards user eye to measure properties of an eye instead of the probe. In yet on other example the measurement device is used to capture picture of an eye/retina of the eye from aligned distance. In such example a camera optics/camera might be attached to the supporting structure instead of the probe.

Optionally, the housing, the optical component, and the angle barrier means are arranged to block visibility of the second light source along the principal axis at a distance superior to d2', wherein d2' is greater than d1'. The virtual image of the second light source is visible till a distance d2', wherein the distance d2' is a finite distance. A distance superior to the distance d2 and less than the distance d2' forms a visibility range of the virtual image of the second light source, wherein the visibility range lies along the principle axis of the optical component.

It will be appreciated that the visibility ranges of the first and second light source are not constant (namely, fixed) and can be varied as per requirement by the user and/or use of the measurement instrument.

As mentioned previously, the optical component is positioned at the first end of the housing. In addition, the housing encompasses the angle barrier means within the hollow structure thereof. Moreover, the housing has a structure that is compatible with requirements of the measurement instrument and/or the user thereof.

Furthermore, the housing, the optical component, and the angle barrier means are arranged to:
block visibility of the first light source along the principal axis at the distance superior to d1'; and
block visibility of the second light source along the principal axis at the distance smaller than d2, wherein d2 is smaller than d1'.

Notably, the housing is structured in a way that limits a viewing angle, tilting to angle and so forth associated with the user for looking through the optical component. The angle barrier means is configured to allow visibility of the first light source until the distance d1' on the principal axis. Also, the angle barrier means is configured to allow visibility of the second light source at a distance superior to the distance d2, wherein d2 is smaller than d1'. Therefore, the first and second light sources have overlapping visibility ranges at a distance superior to d2 and smaller than d1'.

Moreover, the first light is not visible at a distance superior to d1', the second light is not visible at a distance less than d2. Additionally, d1 is less than d2 which is less than d1'. Therefore, the first and the second light sources are visible along principal axis at a distance superior to distance d2 and smaller than distance d1'. In an example, visibility of the first light source and the second light sources indicates a desired alignment with the measurement instrument. In such an example, visibility of only the first light source indicates that the user is too close to the measurement instrument. Moreover, visibility of only the second light source indicates that the user too far from the alignment means. In such an instance, position of the measurement instrument and/or the user is varied to achieve the desired alignment.

Optionally, distance at which the desired alignment is achieved is operational distance for the measurement instrument. More optionally, the operational distance is different for different measurement instruments depending upon an operation thereof and/or requirement of a user using the measurement instrument.

In an example, a measurement instrument may have an operational distance for desired alignment thereof when only first light is visible. In another example, a measurement instrument may have an operational distance for desired alignment when only second light is visible.

In an exemplary implementation, the alignment means of the measurement instrument may be implemented with two light sources, specifically the first light source and the second light source. The optical component may be configured to form virtual images of the first and second light sources. A user of the measurement instrument may view the virtual images of the first and second light sources through the optical component. In addition, the user may view the virtual images of the first and second light sources only within visibility ranges thereof. Moreover, the angle barrier means is configured to limit view of the first and second light sources through the optical component by blocking viewing path of the user. The housing, the optical and the angle barrier means may be arranged to block visibility of the first light source, through the optical component, at a distance superior to a distance d1'. In addition, the alignment means may allow visibility of the second light source at a distance superior to d2, wherein d2 is less than d1'. The user may be required to view both the virtual images of the first and second light sources for achieving the desired alignment. Consequently, an overlapping portion of the viewing zones of the first and second light sources may form an operational distance for the alignment means.

In another exemplary implementation, an alignment means for a measurement instrument may be implemented with two colored light sources, specifically a first colored light source that may be a red colored light and a second colored light source that may be green in color. The optical component may be configured to form virtual images of the first and second colored light sources. A user of the measurement instrument may view the virtual images of the first and second colored light sources through the optical component. In addition, the user may view the virtual images of the first and second colored light sources only within visibility ranges thereof. In addition, the housing, the optical and the angle barrier means may be arranged to block visibility of the first colored light source, through the optical component at a distance superior to a distance d1'. Moreover, the angle barrier means may be configured to block visibility of the second colored light source at a distance superior to distance d2', wherein d2' is less than the distance d1'. The first colored light source and the second colored light source may not have any overlapping visibility ranges. Also, the visibility ranges of the first colored light source and the second colored light source may have a no light zone therebetween where none of the first and second light source is visible. Therefore, at any instance zero or any one of the first and second colored light source may be visible to the user through the optical component. In addition, visibility of the second colored light source may indicate that the user is too far from the alignment means and visibility of the first colored light source may indicate that the user is too near to the alignment means. Therefore, the no light zone between the visibility regions of the first and second colored light sources form an operational distance for correct functioning of the measurement instrument.

In an example, the virtual images of the first and second light sources may appear to be overlapping or not visible to the user. In such an example, an aberration from the desired alignment may be observed by the user.

Optionally, an overlapping or invisibility of lights within the operational distance indicates aberration (namely, deviation) from the desired alignment. In an instance, when there is horizontal aberration, the second light source is viewed partly behind an upper portion of the first light source and a non-light zone between the first light source and the second light source is observed by the user. In another instance, when there is vertical aberration, the second light source is viewed partly behind a side (namely, left, or right) portion of the first light source and a non-light zone between the first light source and the second light source is observed by the user.

In an example when the desired alignment is achieved, the virtual images of the first and second light sources are visible to the user through the optical component. In addition, a non-light zone is observed by the user.

Optionally, the desired alignment is achieved with the first, second and optional third light sources. A virtual image of the third light source is created by the optical component behind the focal point. The virtual image of the third light source is visible after a distance superior to distance d3 and till a distance d3'. More optionally, the distance d3' is finite.

Optionally, the housing, the optical component, and the angle barrier means are arranged to: block visibility of the third light source along the principal axis at a distance smaller than d3, wherein d3 is greater than d1' and smaller than d2'. The angle barrier means allows for visibility of the third light source along the principal axis within a visibility range thereof. The third light source is not visible prior to the distance d3. In addition, the first, second and optional third light source are visible at a distance superior to d3 and smaller than d2'. The distance superior to d3 and smaller than d2' is the operational distance for the measurement instrument comprising the first, second and the third light source. However, the operational distance can be changed based upon an operation of the measurement instrument and/or user of thereof.

In an example, the operational distance may be a distance between d2 and d1' wherein the first and second light sources are visible. In another example, the operational distance may be a distance wherein only the second light source is visible.

In an exemplary implementation, an alignment means for a measurement instrument may be implemented with three light sources, specifically a first light source, a second light source and a third light source. The optical component of the alignment means may be configured to form virtual images of the first, second and optional third light sources. A user of the measurement instrument may view the virtual images of the first, second and optional third light sources through the optical component. In addition, the user may view the virtual images of the first, second and third light sources only within visibility ranges thereof. Moreover, the housing, the optical component and the angle barrier means are arranged to limit view of the first, second and third light sources through the optical component by blocking viewing path of the user. Specifically, visibility of the first light source, at a distance superior to a distance d1' may be blocked. In addition, visibility of the second light source, through the optical component, at a distance smaller than d2 and superior to d2' may be blocked, wherein d2 is smaller than d1' and d1' is smaller than d2'. Therefore, the first and second light sources have an overlapping viewing zone. Furthermore, the optical barrier disk is configured to allow visibility of the third light source at a distance superior to d3, wherein d3 is greater than d2'. The user may be required to view the virtual image of the second light source for achieving the desired alignment. Consequently, a distance superior to d1' and smaller than d3 including visibility range of only the second light source may form an operational distance for the alignment means.

Furthermore, the present disclosure relates to the measurement instrument comprising the alignment means. The measurement instrument is configured to achieve the desired alignment by way of the alignment means. Specifically, the alignment means is operatively coupled to the measurement instrument. Optionally, a position of the measurement instrument and/or the user is changed to achieve the desired alignment.

The present disclosure relates to a method of aligning the measurement instrument using the alignment means comprising adjusting the visibility range of the first light source until the first distance S1 from the optical component. The method of aligning the measurement instrument using the alignment means further comprises adjusting a visibility range of the second light source to start from the second distance S2 from the optical component, the second distance S2 being smaller than the first distance S1. Furthermore, the first and second light sources are used for arranging the measurement instrument to achieve a desired distance of eye of the user from the measurement instrument. In addition, the first and second light sources are used for adjusting a horizontal and/or vertical position of the eye to achieve the desired alignment.

Further the present disclosure provides a measurement instrument comprising an alignment means as described earlier. Optionally the measurement instrument is an instrument for measuring a pressure of an eye. Further optionally the measurement instrument comprises a probe configured to be ejected towards the eye to measure the pressure of the eye.

DETAILED DESCRIPTION OF THE DRAWINGS

Referring to FIG. 1, there is shown a schematic illustration of an alignment means 100 of a measurement instrument 102, in accordance with an embodiment of the present disclosure. The alignment means 100 comprises a housing 104. The alignment means 100 comprises an optical component 106 having a principal axis in a direction parallel to a desired alignment. The alignment means 100 comprises a first light source 108 and a second light source 110. The first light source 108 is positioned at a first distance S1 from the optical component 106 and the second light source 110 is positioned at a second distance S2 from the optical component 106. The first light source 108 and the second light source 110 are arranged to provide light towards the optical component 106. The alignment means 100 comprises an angle barrier means 112 arranged between the optical component 106, and the first and second light sources 108 and 110 respectively. The alignment means includes a supporting structure. The supporting structure comprises an inner supporting structure part 114 and an outer supporting structure part 118. An optional probe 116 is arranged to move in a backward and forward direction inside the inner and outer supporting structures 114, 118 to measure properties of an eye 120.

FIG. 1 is merely an example, which should not unduly limit the scope of the claims herein. It is to be understood that the specific designation for the alignment means 100 is provided as an example and is not to be construed as limiting the alignment means 100 to specific numbers, types, or arrangements of optical components, light sources, and angle barrier means. A person skilled in the art will recognize many variations, alternatives, and modifications of embodiments of the present disclosure.

Figure 2:
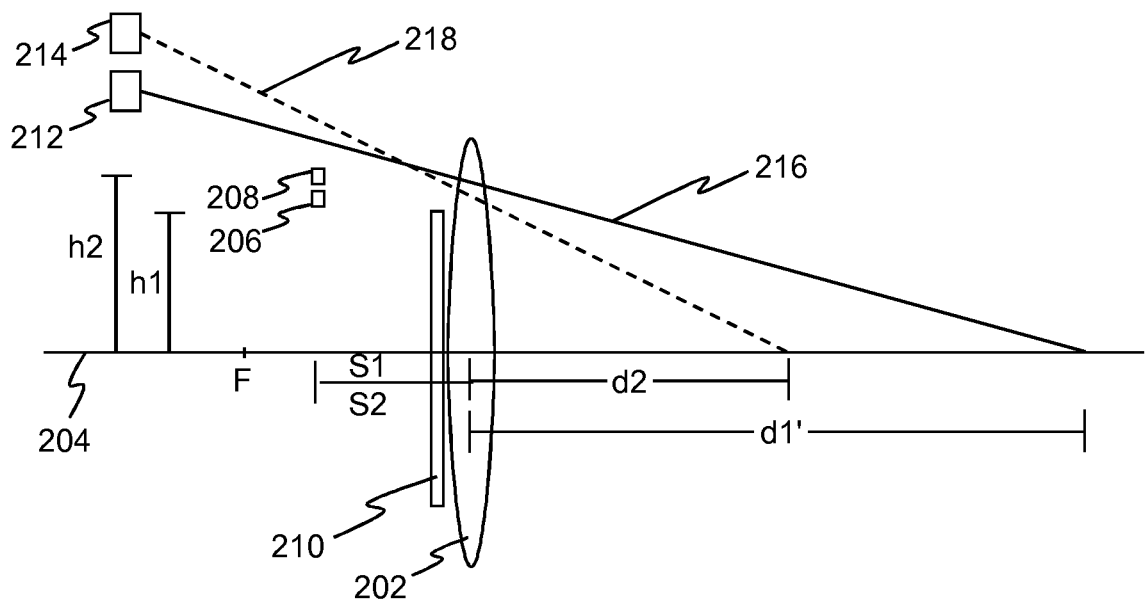
FIG. 2 is a schematic illustration of an implementation of the alignment means, in accordance with an embodiment of the present disclosure.

Referring to FIG. 2, there is shown a schematic illustration of an implementation of an alignment means (such as the alignment means 100 of FIG. 1), in accordance with an embodiment of the present disclosure. As shown, the alignment means includes an optical component 202 having a principal axis 204 in a direction parallel to a desired alignment. Furthermore, a first light source 206 is positioned at a first height h1 from the principle axis 204. In addition, a second light source 208 is positioned at a second height h2 from the principle axis 204. The first light source 206 and the second light source 208 are positioned between the optical component 202 and a focal point F of the optical component 202 at a distance S1 and S2 from the optical component 202 respectively. In a FIGS. 51 and S2 are equal. Furthermore, an angle barrier means 210 is arranged between the optical component 202, and the first light source 206 and second light source 208.

It will be appreciated that light from the first light source 206, passes through the optical component 202 and creates a virtual image 212 of the first light source 206. Similarly, light from the second light source 208, passes through the optical component 202 and creates a virtual image 214 of the second light source 208. Furthermore, housing (such as the housing 104 as shown in FIG. 1), the optical component 202, and the angle barrier means 210 are arranged to block visibility of the first light source 206 at a distance superior to distance d1' along the principal axis 204. Moreover, the housing, the optical component 202, and the angle barrier means 210 are arranged to block visibility of the second light source 208 at a distance smaller than d2 along the principal axis 204.

For illustration purposes, a first line marker 216 extending from the virtual image 212 of the first light source 206, to the principal axis 204 illustrates a distance d1' until which the first light source 206 is visible. Similarly, a second line marker 218 extending from the virtual image 214 of the second light source 208, to the principal axis 204 illustrates a distance d2 after which the second light source 208 is visible FIG. 2 is merely an example, which should not unduly limit the scope of the claims herein. It is to be understood that the specific designation for the implementation of alignment means is provided as an example and is not to be construed as limiting the alignment means to specific numbers, types, or arrangements of optical components, light sources, and angle barrier means. Furthermore, in FIG. 2, the first light source 206 and the second light source 208 are considered to be positioned at an equal distance from the optical component 202. A person skilled in the art will recognize many variations, alternatives, and modifications of embodiments of the present disclosure.

Figure 3:
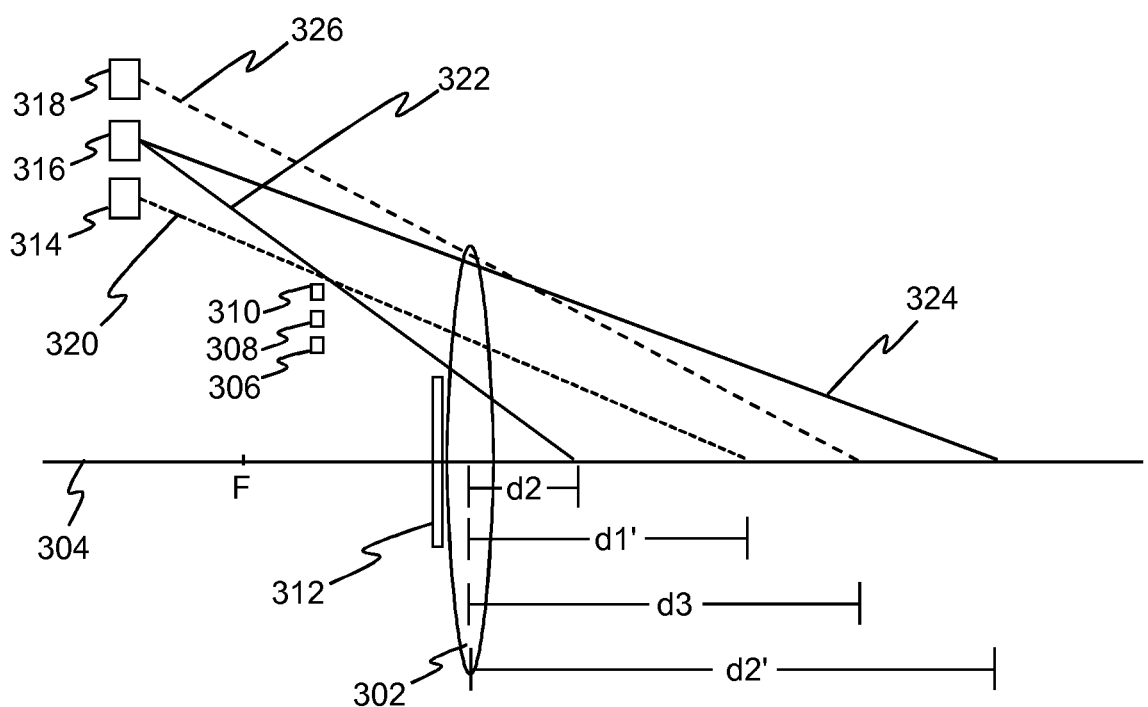
FIG. 3 is a schematic illustration of an exemplary implementation of an alignment means, in accordance with an embodiment of the present disclosure.

Referring to FIG. 3, there is shown a schematic illustration of an exemplary implementation of an alignment means, in accordance with an embodiment of the present disclosure. As shown, the alignment means includes an optical component 302 having a principal axis 304 in a direction parallel to a desired alignment. Furthermore, a first light source 306 is positioned at a first height h1 (not shown) from the principle axis 304. In addition, a second light source 308 is positioned at a second height h2 (not shown) from the principle axis 304. Furthermore, a third light source 310 is positioned at a third height h3 (not shown) from the principle axis 304. The first light source 306, the second light source 308 and the third light source 310 are positioned between the optical component 302 and a focal point F of the optical component 302. Furthermore, an angle barrier means 312 is arranged between the optical component 302, and the first light source 306, second light source 308 and the third light source 310.

It will be appreciated that light from the first light source 306, passes through the optical component 302 and creates a virtual image 314 of the first light source 306. Similarly, light from the second light source 308, passes through the optical component 302 and creates a virtual image 316 of the second light source 308. Also, light from the third light source 310, passes through the optical component 302 and creates a virtual image 318 of the third light source 310. Furthermore, housing (such as the housing 104 as shown in FIG. 1), the optical component 302, and the angle barrier means 312 are arranged to block visibility of the first light source 306 at a distance superior to distance d1' along the principal axis 304. Moreover, the housing, the optical component 302, and the angle barrier means 312 are arranged to block visibility of the second light source 308 at a distance smaller than d2 and at a distance superior to d2', along the principal axis 304. Furthermore, the housing, the optical component 302, and the angle barrier means 312 are arranged to block visibility of the third light source 310 at a distance smaller than d3.

For illustration purposes, a first line marker 320 extending from the virtual image 314 of the first light source 306, to the principal axis 304 illustrates a distance d1' until which the first light source 306 is visible. Similarly, a second line marker 322 and a third line marker 324 extending from the virtual image 316 of the second light source 308, to the principal axis 304 illustrate a distance d2 after which the second light source 308 is visible and a distance d2' until which the second light source 308 is visible, respectively. Also, a fourth line marker 326 extending from the virtual image 318 of the third light source 310, to the principal axis 304 illustrate a distance d3 after which the third light source 310 is visible.

Figure 4A:
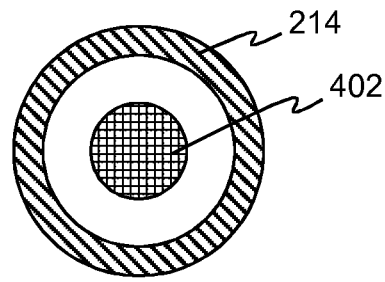
FIGS. 4A, 4B and 4C is an exemplary operation of the alignment means with respect to an eye of a user, in accordance with an embodiment of the present disclosure.
Figure 4B:
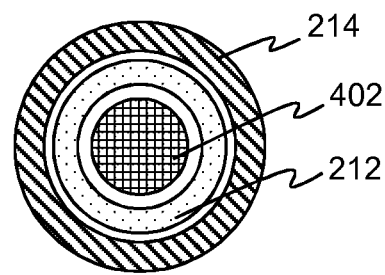
Figure 4C:
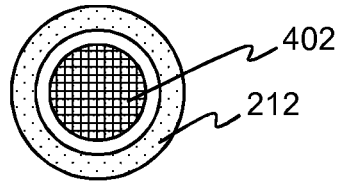

Referring to FIGS. 4A, 4B and 4C, there is shown an exemplary operation of an alignment means (such as the alignment means 100 of FIG. 1) with respect to an eye of a user, in accordance with an embodiment of the present disclosure. The alignment means is implemented in a similar manner as described in FIG. 2. Notably, the eye of the user is aligned with the principal axis of the optical component (such as the principal axis 204 of the optical component 202 of FIG. 2). The virtual images 212 and 214 of the first light source 206 (of FIG. 2) and the second light source 208 (of FIG. 2) respectively, are optionally centered around a probe 402 (such as the probe 116 of FIG. 1). Furthermore, the alignment means is configured to facilitate in achieving a desired alignment between the measurement instrument 102 and the eye of the user (specifically, a desired distance of the eye from the measurement instrument 102).

In FIG. 4A, the eye of the user is positioned at a distance superior to d1'. Therefore, only the virtual image 214 of the second light source 208 is visible to the eye of the user through the optical component.

In FIG. 4B, the eye of the user is positioned at a distance superior to d2 and smaller than d1'. Therefore, the virtual images 212 and 214 of the first light source 206 and the second light source 208 respectively, are visible to the eye of the user through the optical component.

In FIG. 4C, the eye of the user is positioned at a distance smaller than d2. Therefore, only the virtual image 212 of the first light source 206 is visible to the eye of the user through the optical component It will be appreciated that the eye of the user is positioned at a desired distance with respect to the measurement instrument when the virtual images 212 and 214 of the first light source 206 and the second light source 208 respectively, are visible to the eye of the user (as illustrated in FIG. 4B). However, when only the virtual image 214 of the second light source 208 is visible to the eye of the user (as illustrated in FIG. 4A), the user is positioned far with respect to the measurement instrument. Similarly, when only the virtual image 212 of the first light source 206 is visible to the eye of the user (as illustrated in FIG. 4C), the user is positioned near the measurement instrument Referring to FIGS. 5A, 5B and 5C, there is shown an exemplary operation of an alignment means (such as the alignment means 100 of FIG. 1) with respect to an eye of a user, in accordance with an embodiment of the present disclosure. The alignment means is implemented in a similar manner as described in FIG. 2. Notably, the eye of the user is positioned at a desired distance from the measurement instrument (such as the measurement instrument 102 of FIG. 1). The virtual images 212 and 214 of the first light source 206 (of FIG. 2) and the second light source 208 (of FIG. 2) respectively, are optionally centered around a probe 402 (such as the probe 116 of FIG. 1). Furthermore, the alignment means is configured to facilitate in achieving a desired alignment between the measurement instrument 102 and the eye of the user (specifically, a desired vertical and horizontal alignment of the eye with respect to the measurement instrument 102).

Figure 5A:
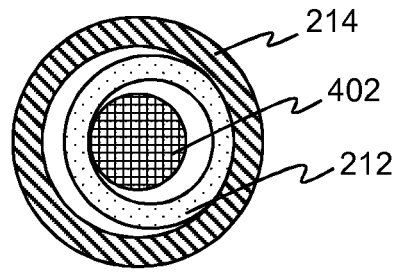
FIGS. 5A, 5B and 5C is an exemplary operation of the alignment means with respect to the eye of the user, in accordance with an embodiment of the present disclosure.

In FIG. 5A, the eye of the user is horizontally misaligned with respect to the measurement instrument 102. Therefore, the virtual image 214 of the second light source 208 partially overlaps the virtual image 212 of the first light source 206 in a horizontal direction.

Figure 5B:
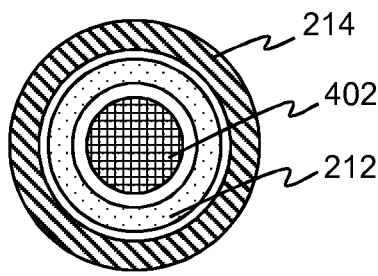

In FIG. 5B, the eye of the user is in the desired vertical and horizontal alignment with respect to the measurement instrument 102. Therefore, the virtual image 214 of the second light source 208 and the virtual image 212 of the first light source 206 are substantially centered.

Figure 5C:
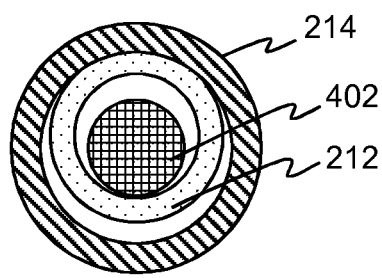

In FIG. 5C, the eye of the user is vertically misaligned with respect to the measurement instrument 102. Therefore, the virtual image 214 of the second light source 208 partially overlaps the virtual image 212 of the first light source 206 in a vertical direction.

Figure 6A:
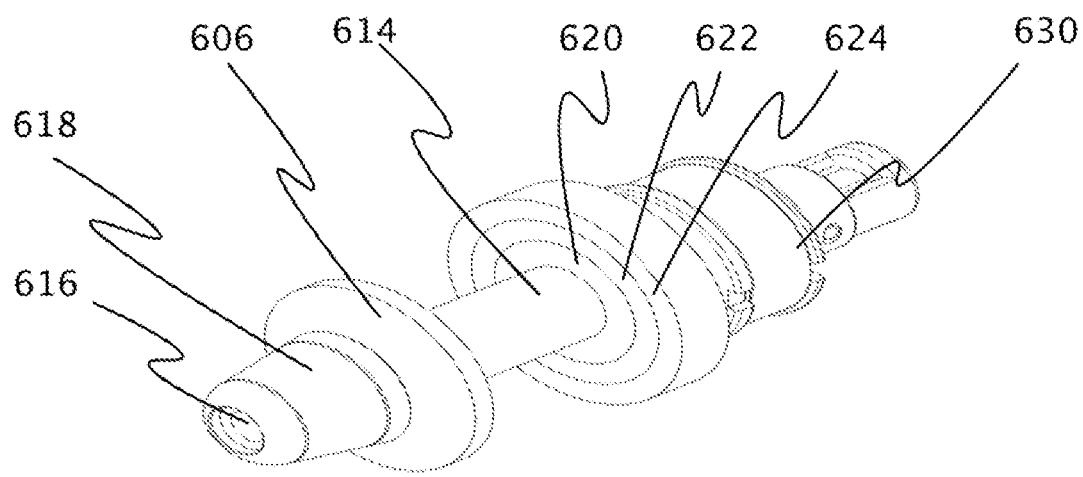
FIGS. 6A and 6B is a schematic illustration of an implementation of an alignment means in accordance with an embodiment of the present disclosure.
Figure 6B:
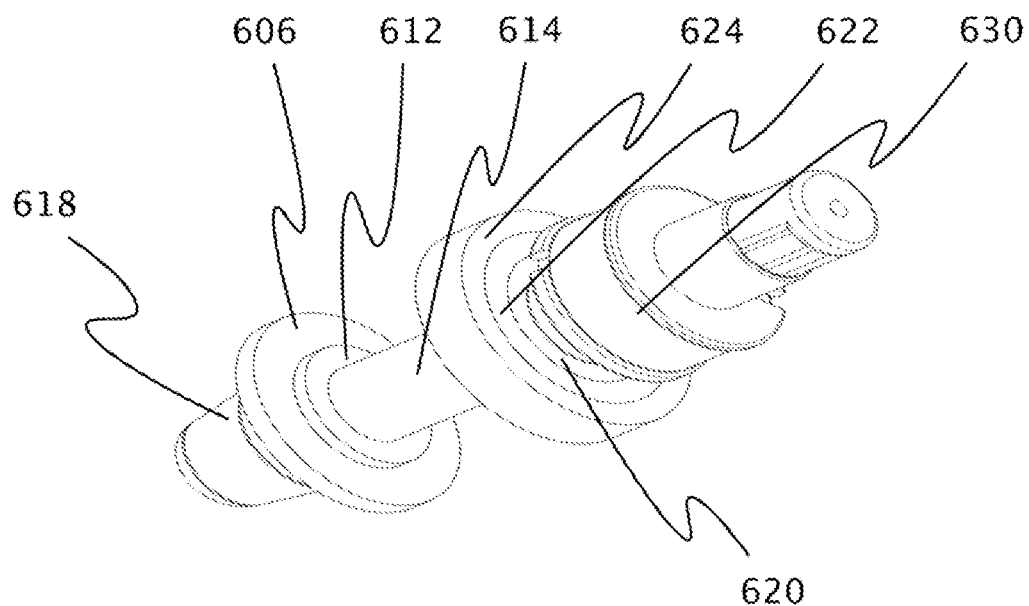

In FIG. 6A is a perspective illustration of an alignment means as seen from a front and FIG. 6B is a perspective illustration the alignment means as seen from a behind, in accordance with an embodiment of the present disclosure. The alignment means comprises an optical component 606 having a principal axis in a direction parallel to a desired alignment. The alignment means comprises a first light source 620, a second light source 622 and a third light source 624. The light sources are in the example circular light sources. The light sources are arranged at an equal distance from the optical component 606. The circular light sources comprises a circular light guide and a LED (not shown) providing light for respective light guide. The first circular light guide of the first light source 620 has a radius of h1. The second circular light guide of the second light source 622 has a radius of h2. The third circular light guide of the third light source 624 has a radius of h3. The radius h1 is smaller than the radius h2. The radius h2 is smaller than the radius h3. The light guides emit different colors of light (or alternatively for example flash with dedicated patterns to person to identify between the light guides). The light sources 620, 622, 624 and the optical component 606 are arranged around inner supporting structure part 614. The inner supporting structure in given example is a hollow tube. An optional probe 616 is configured to be ejected towards user eye when a measurement instrument having the alignment means is used to measure properties of an eye. The probe 616 is partly covered with outer supporting structure 618. The probe 616 is ejected/controlled/held with an optional coil arrangement 630 arranged around the inner supporting structure part 614. An angle barrier means 612 is arranged between the optical component 606 and the light sources. The angle barrier means 612 of example of FIGS. 6A and 6B is an angle barrier disk.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. An alignment means of a measurement instrument, the alignment means comprising
   a housing;
   an optical component having a principal axis in a direction parallel to a desired alignment, the optical component being configured such that an eye of the user is to be aligned with the principal axis of the optical component;

a first light source positioned at a first distance S1 from the optical component and at a first height h1 from the principle axis;

a second light source positioned at a second distance S2 from the optical component and at a second height h2 from the principle axis; and an angle barrier means, wherein the optical component comprises a focal point, wherein the first and second light sources are positioned between the optical component and the focal point; and wherein the housing, the optical component, and the angle barrier means are arranged to:

block visibility of the first light source along the principal axis at a distance superior to d1';

block visibility of the second light source along the principal axis at a distance smaller than d2, wherein d2 is smaller than d1', and wherein d1' and d2 are distances from the optical component; and block visibility of the second light source along the principal axis at a distance superior to d2', wherein d2' is greater than d1';

the alignment means further comprising a third light source arranged at a third distance S3 from the optical component and at a third height h3 from the principal axis, wherein the housing, the optical component, and the angle barrier means are arranged to block visibility of the third light source along the principal axis at a distance smaller than d3, and wherein d3 is greater than d1' and smaller than d2'.

2. An alignment means according to claim 1, wherein each of the first, second and optional third light sources are arranged to provide a differently coloured light.

3. An alignment means according to claim 1, wherein at least one of the first, second and optional third light source is a blinking light source.

4. An alignment means according to claim 1, wherein at least one of the first, second and optional third light source is a circular light source.

5. An alignment means according to claim 1, wherein each of the first, second and optional third light sources are implemented by way of a light emitter and a light guide.

6. An alignment means according to claim 5, wherein the light emitter is a light emitting diode.

7. An alignment means according to claim 5, wherein the light guide is one of a circular light guide, a triangular light guide, an oval light guide, a square light guide, a line light guide.

8. An alignment means according to claim 1, wherein the angle barrier means are arranged between the optical component, and the first and second light sources.

9. An alignment means according to claim 1, wherein the optical component is arranged between the angle barrier means and the first and the second light sources.

10. An alignment means according to claim 1 wherein the angle barrier means is an angle barrier disk.

11. An alignment means according to claim 1 wherein the angle barrier means is a supporting structure or housing.

12. A measurement instrument comprising an alignment means according to claim 1.

13. A measurement instrument according to claim 12, wherein the measurement instrument is an instrument for measuring a pressure of an eye.

14. A measurement instrument according to claim 13, wherein the measurement instrument comprises a probe configured to be ejected towards the eye to measure the pressure of the eye.

* * * * *